(12) United States Patent
Regan et al.

(10) Patent No.: US 9,855,416 B1
(45) Date of Patent: Jan. 2, 2018

(54) MAGAZINE HOLDING PLURAL ELECTRODE-CARRYING APPLICATORS

(71) Applicant: Rhythmlink International, LLC, Columbia, SC (US)

(72) Inventors: Shawn V. Regan, Columbia, SC (US); Daniel Smith, Lexington, SC (US)

(73) Assignee: Rhythmlink International LLC, Columbia, SC (US)

( * ) Notice: Subject to any disclaimer, the term of this patent is extended or adjusted under 35 U.S.C. 154(b) by 684 days.

(21) Appl. No.: 14/465,267

(22) Filed: Aug. 21, 2014

Related U.S. Application Data

(60) Provisional application No. 61/868,350, filed on Aug. 21, 2013.

(51) Int. Cl.
- *A61B 19/00* (2006.01)
- *A61N 1/05* (2006.01)
- *A61B 17/34* (2006.01)
- *A61B 5/04* (2006.01)

(52) U.S. Cl.
CPC ........ *A61N 1/0504* (2013.01); *A61B 5/04001* (2013.01); *A61B 17/3468* (2013.01)

(58) Field of Classification Search
CPC ...... A61N 1/05; A61N 1/0502; A61N 1/0504; A61N 1/0551; A61N 1/3605; A61B 5/04001; A61B 5/0476; A61B 5/0488; A61B 5/0442; A61B 5/04; A61B 5/04002; A61B 5/04004; A61B 17/3468; A61M 37/0069
USPC ......... 227/175.1, 175.2, 175.3, 175.4, 176.1, 227/178.1; 606/129, 170; 607/115, 116; 600/373, 377; 221/92, 93, 99, 242, 185, 221/281
See application file for complete search history.

(56) References Cited

U.S. PATENT DOCUMENTS

| | | | |
|---|---|---|---|
| 5,281,197 A * | 1/1994 | Arias | A61M 37/0069 604/209 |
| 6,277,102 B1 * | 8/2001 | Carilli | A61M 5/1782 604/240 |
| 8,694,070 B2 | 4/2014 | Wilson | |
| 2009/0163889 A1 * | 6/2009 | Cauller | A61B 5/6849 604/506 |
| 2012/0179062 A1 * | 7/2012 | Wilson | A61B 5/0478 600/544 |
| 2013/0158600 A1 * | 6/2013 | Conklin | A61B 17/0401 606/232 |

* cited by examiner

*Primary Examiner* — Jonathan Miles
*Assistant Examiner* — Majid Jamialahmadi
(74) *Attorney, Agent, or Firm* — Nexsen Pruet, LLC; Michael A. Mann

(57) ABSTRACT

A system for inserting a series of subdermal electrodes into the skin of a patient for neurological monitoring includes a magazine with an interior, a first end and an opposing second end. The first end has an opening. A row of applicators are carried in the interior of the magazine, parallel the its major axis. The first applicator presents itself at the opening in the first end and is followed in turn by a subsequent applicator. Each applicator carries an electrode that is ejected from that applicator when an applicator is pressed against the skin of a patient. The magazine has an actuator that advances each applicator in sequence toward the opening of the magazine to expel them one at a time after each ejects its electrode.

8 Claims, 9 Drawing Sheets

MAGAZINE HOLDING PLURAL ELECTRODE-CARRYING APPLICATORS

PRIORITY CLAIM

The priority benefit of U.S. provisional patent application, Ser. No. 61/868,350, filed Aug. 21, 2013, is claimed.

DETAILED DESCRIPTION OF PREFERRED EMBODIMENTS

The present invention is a system for inserting a series of subdermal electrodes into the skin of a patient for neurological monitoring. This system comprises a magazine with an interior, a major axis and a first end and an opposing second end. The first end has an opening. Plural applicators are carried in the interior of the magazine in a row and in parallel with the major axis of the magazine. The plural applicators include a previous applicator followed by a subsequent applicator. The previous applicator has a first end and an opposing second end. The subsequent applicator has a first end and a second end, and the first end of the previous applicator presents itself at the opening of the magazine.

The system includes plural electrodes, each of which is releasably carried by one applicator so that the electrode is ejected from that applicator when an applicator is pressed against the skin of a patient. Finally, the system includes an actuator carried by the magazine. The actuator advances the plural applicators in sequence and axially toward the opening of the magazine to expel the previous applicator through the opening and to present the subsequent applicator at the opening.

The system may also include a stopper carried in the magazine at its second end and aligned with the row of plural applicators. The stopper is moveable toward the first end of the magazine but not rearward. The stopper moves in increments so that an applicator is ejected and a subsequent applicator is presented at the opening in each incremental movement.

The stopper has two radially-opposing, radially-biased feet and the magazine has plural catches dimensioned to receive and hold the feet against movement rearward toward the second end of the magazine as the stopper is moved axially forward toward the first end of said magazine. Also, each applicator has a dog and the actuator has a dog-engaging bar that may be moved axially only toward the first end of the magazine and moving both radially outward and axially as the dog-engaging bar is moved toward the second end of the magazine. As it is moved, the dog-engaging bar is cammed by the dog of said applicator.

The actuator also includes a slide carried exterior to the magazine and in operative connection with the dog-engaging bar interior to the magazine to move the applicators.

The magazine has an axial channel, through which the lead wire from each electrode hangs. Finally, each applicator also includes a retention module with a hole in it for holding the electrode, and a plunger that moves with respect to the retention module. This plunger has a pin aligned with the hole in the retention module for ejecting the electrode when the retention module as the pin move toward each other. The plunger has a spring that interacts with the retention module by resisting relative movement of the plunger and the retention module. Accordingly, the plunger loads that spring as the retention module presses against the skin of a patient.

Figure 4:
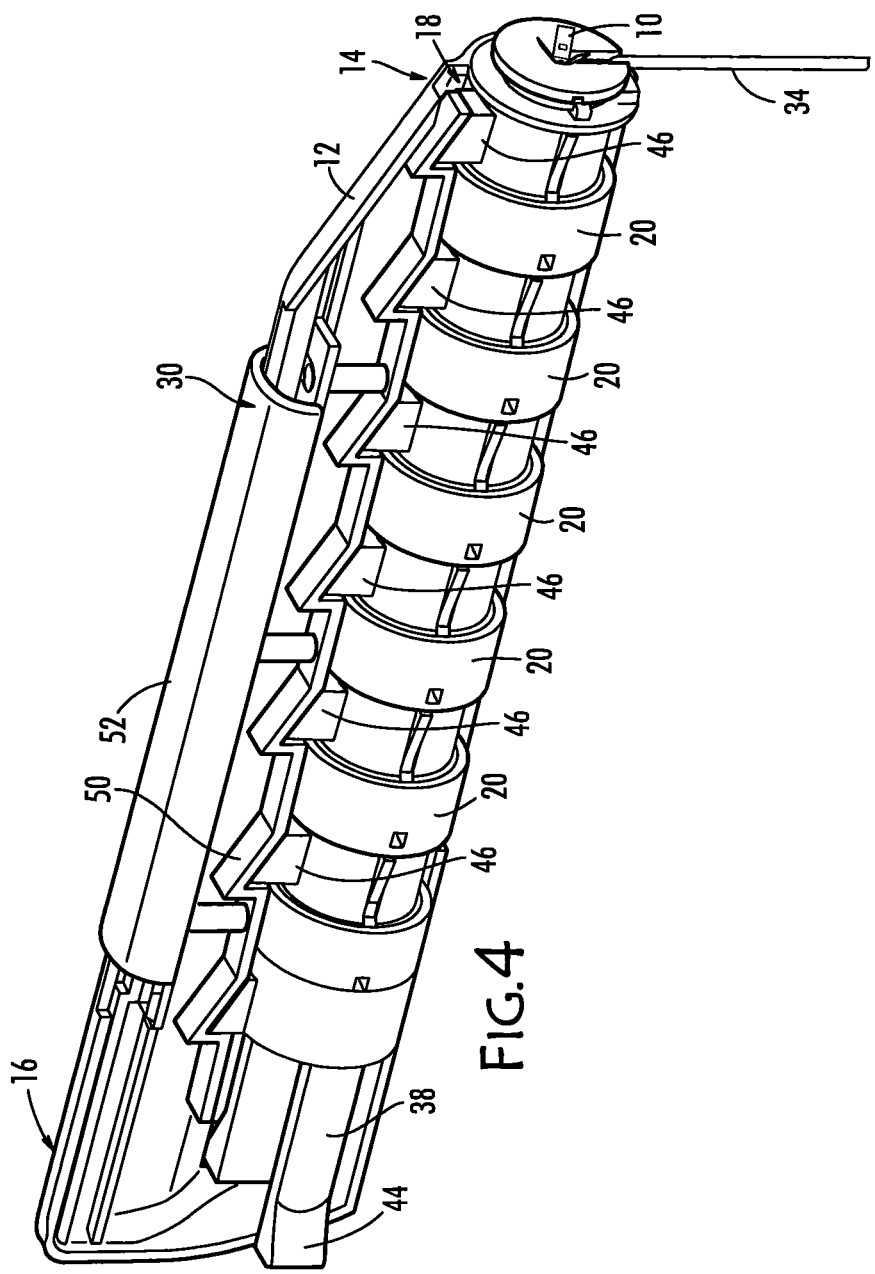
FIG. 4 is a partial, perspective, right side closer view of the present magazine with the electrode ejected from the retention module, according to an embodiment of the invention.

Referring now to the figures, the present invention is a system for inserting a series of subdermal electrodes 10 into the skin of a patient for neurological monitoring. The system includes a magazine 12 with a major axis and a first end 14 and an opposing second end 16. There is an opening 18 in the magazine 12's first end. In the interior of the magazine 12, best seen in FIG. 4, are plural applicators 20 in a row parallel to the axis of the magazine 12 so one leads another except for the last of the applicators 20 which trails the ones before it. Each applicator 20 has a first end 22 and an opposing second end 24. The first end of the previous applicator 20 presents at the opening 18 of the magazine 12.

Figure 1:
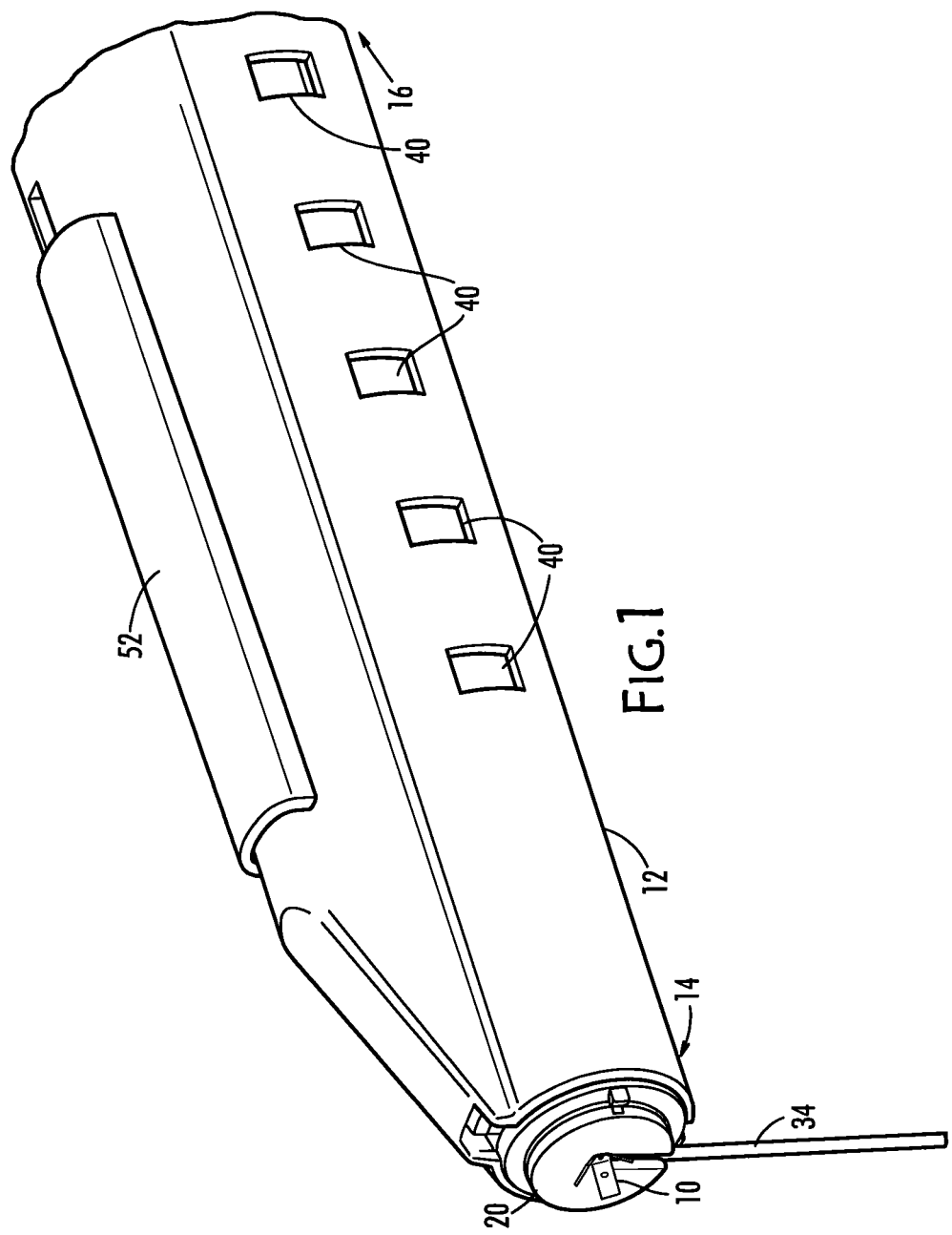
FIG. 1 is a partial, perspective left side view of the present magazine with an applicator according to an embodiment of the invention.
Figure 2:
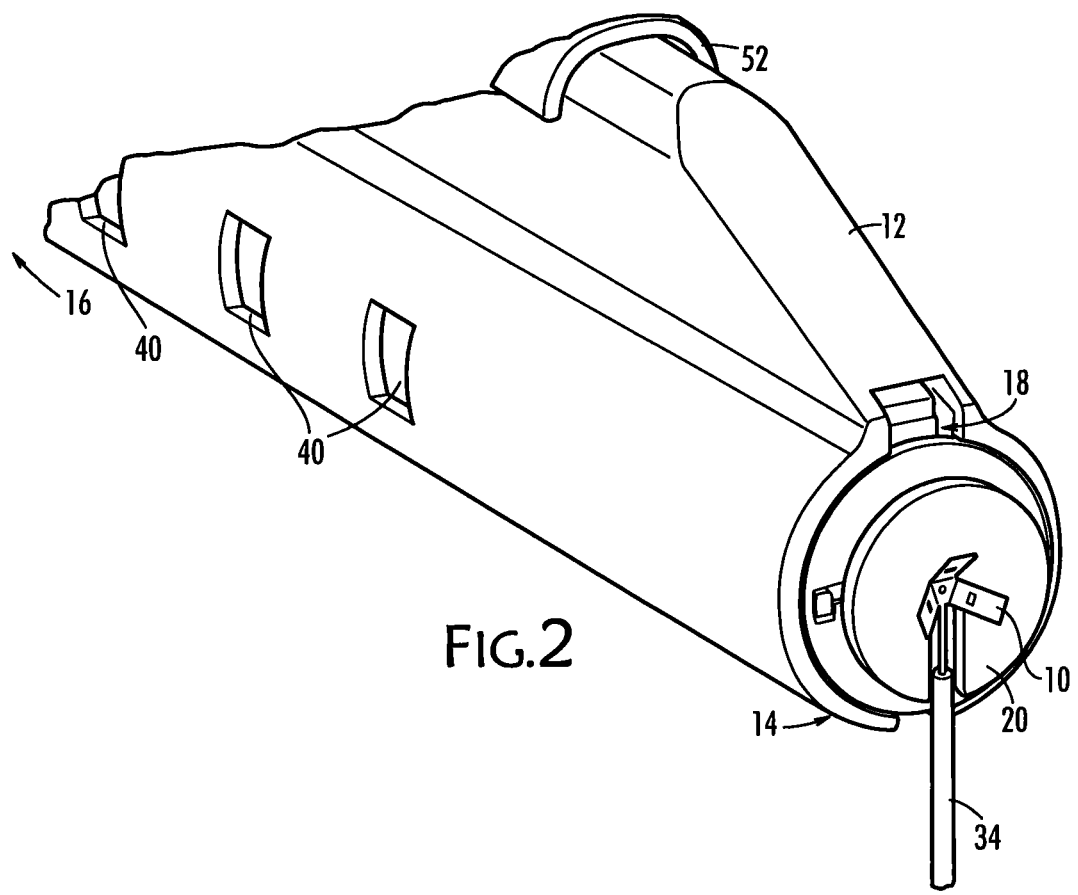
FIG. 2 is a partial, perspective, right side view of the present magazine shown in FIG. 1, according to an embodiment of the invention.
Figure 3:
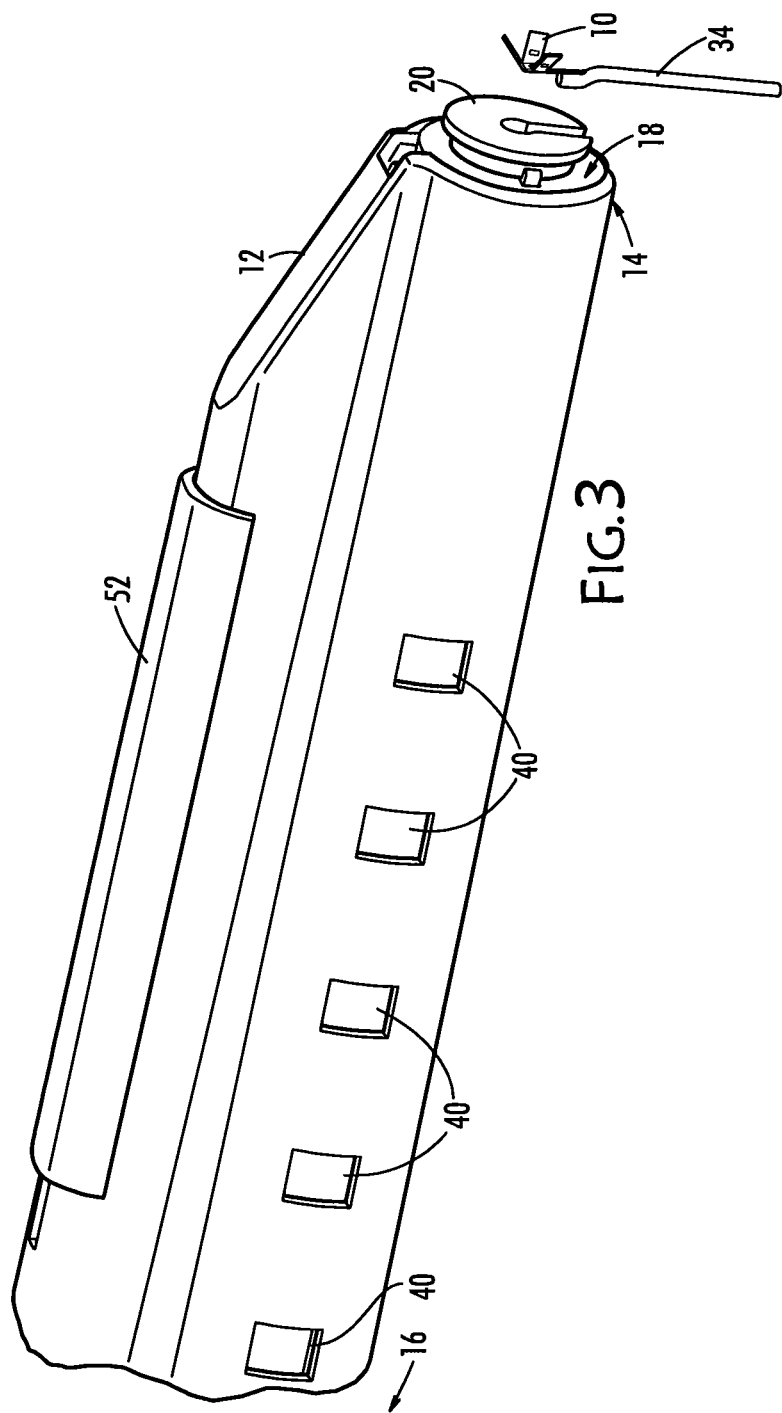
FIG. 3 is a perspective right side partially cut away view of the magazine, according to an embodiment of the invention.
Figure 9:
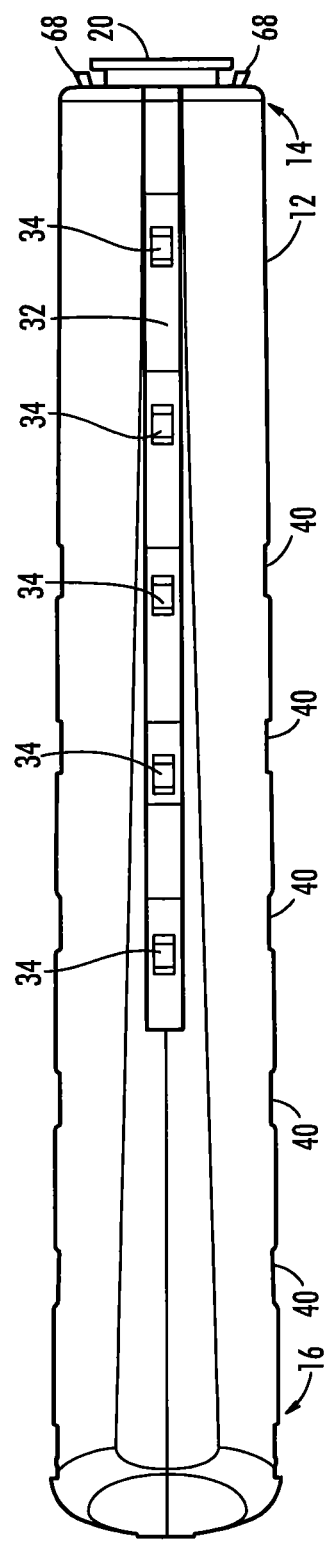
FIG. 9 is a bottom view of the magazine showing the channel for a lead wire according to an embodiment of the invention.

Each applicator 20 releasably carries one electrode 10, as best seen in FIGS. 1-3. The electrode 10 is ejected from the applicator 20 when the applicator 20 is pressed against the skin of a patient. See FIG. 3. The applicators 20 are used in sequence controlled by an actuator 30 carried by the magazine 12 to advance each of the applicators 20 one at a time and axially toward the opening 18 of the magazine 12 where they are expelled after each in turn ejects its electrode 10 into the patient's skin so the next applicator 20 can present at the opening 18 with its electrode 10, ready for application to the patient's skin. See FIG. 4. In addition, the magazine 12 has an axial channel 32 formed through its wall for a lead wire 34 to hang from the electrode 10 carried by each of the applicators 20, as shown in FIG. 9.

The magazine 12 also carries a stopper 38, located toward the second end 16 and aligned with the row of applicators 20. See FIGS. 4 and 8. The stopper 38 is moveable toward the first end 14 of the magazine 12 but not rearward toward the second end 16. Furthermore, the stopper 38 moves in increments. In each increment, the previous applicator 20 is expelled from the magazine 12 so the first end of the subsequent applicator 20 can present at the magazine 12 opening 18. To prevent rearward movement of the stopper 38, the interior of the magazine 12 has plural catches 40 formed in its interior wall and the stopper 38 includes two radially-opposing, radially-biased feet 44. As the stopper 38 is moved forward toward the first end 14 of the magazine 12, its feet 44 find the catches 40 and brace the stopper 38 against rearward movement.

As shown in FIG. 4, each applicator 20 has a "dog" 46 and the actuator 30 has a dog-engaging bar 50 that pushes against the dogs 46 of the applicators 20 to move them axially toward first end 14 of the magazine 12 and its opening 18. If the actuator 30 is moved rearward, toward second end 16 of magazine 12, the applicators 20, prevented from rearward movement by stopper 38, cam the dog-engaging bar 50 radially outward, moving radially with respect to guide posts on slide 52. To move the actuator 30, the exterior slide 52 is in operative connection with the dog-engaging bar 50 on the interior of the magazine 12 for the user to move the applicators 20 axially.

Figure 5:
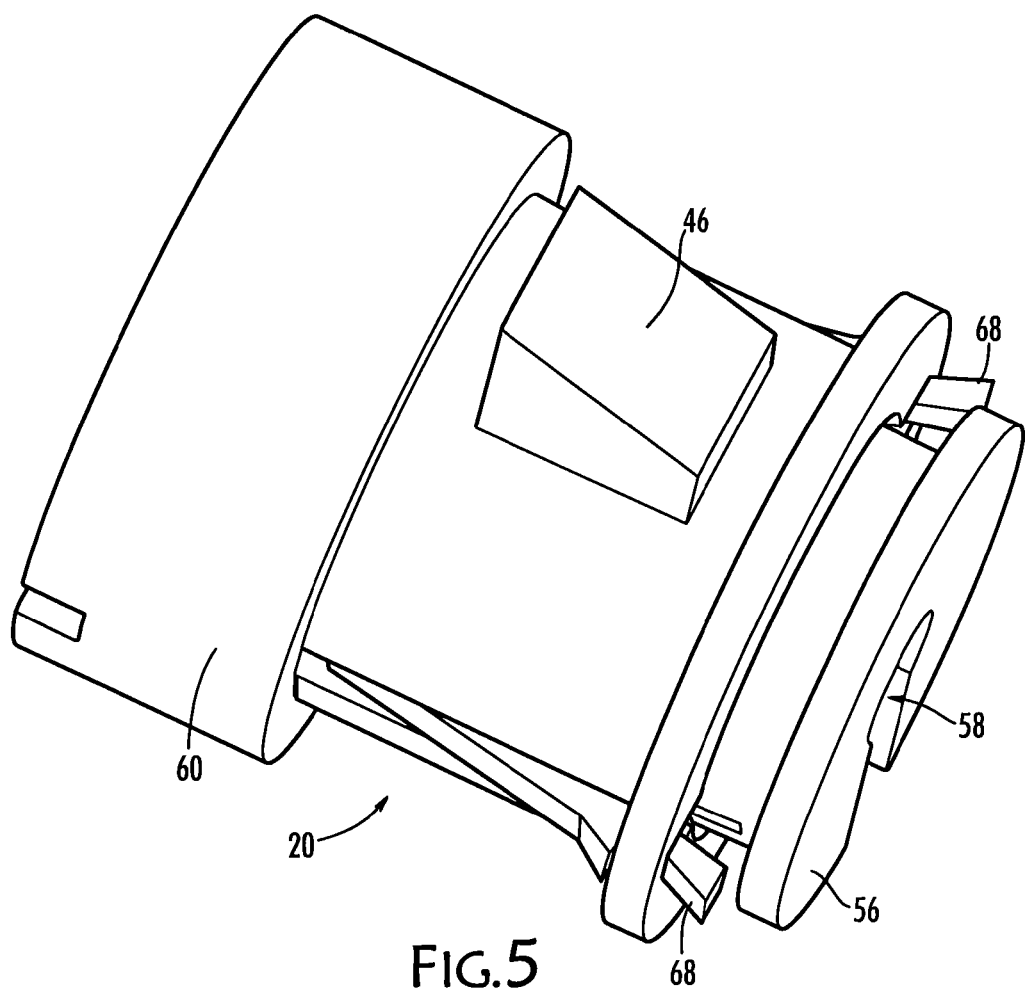
FIG. 5 shows an applicator without an electrode, according to an embodiment of the invention.
Figure 6:
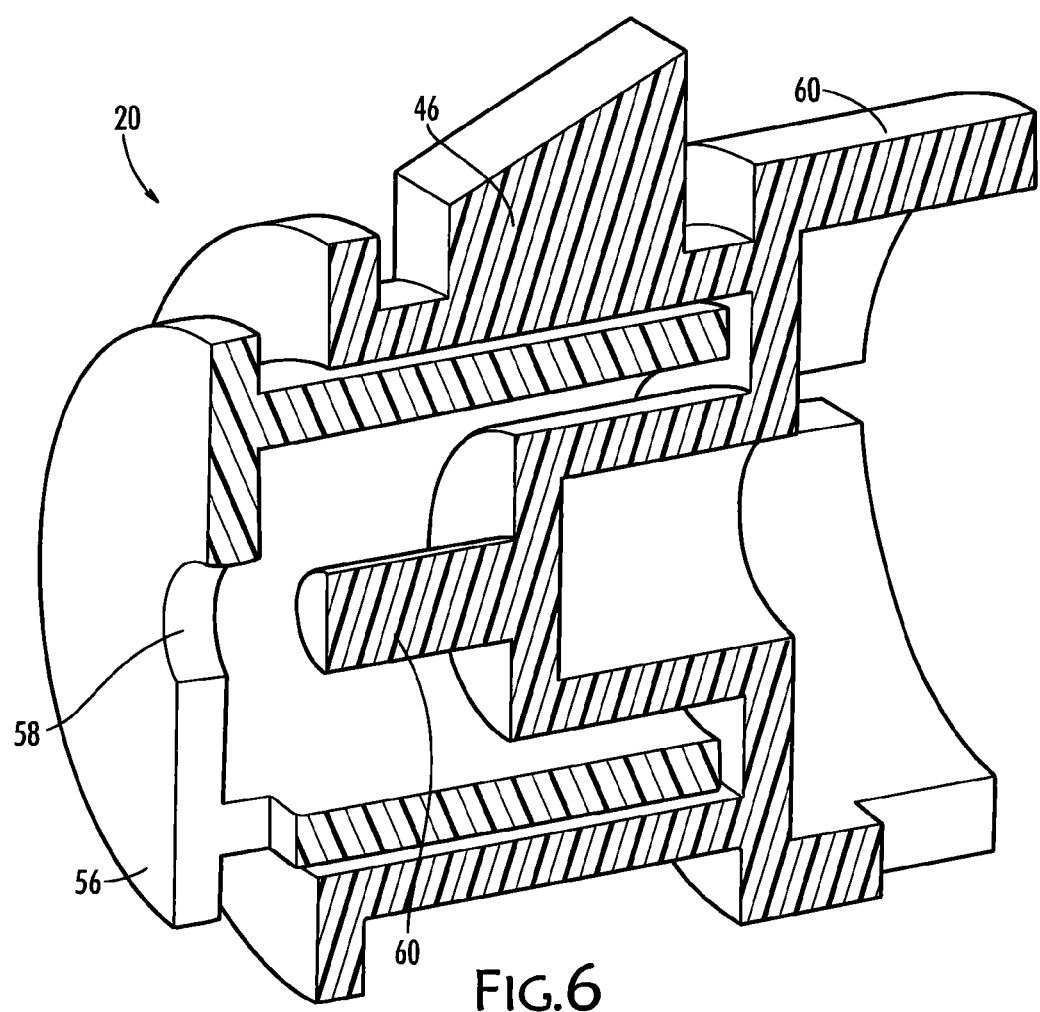
FIG. 6 is a cross sectional view of an applicator, according to an embodiment of the invention.

As best seen in FIGS. 5 and 6, each applicator 20 comprises an electrode retention module 56. The electrode 10 is inserted into a hole 58 in the module 56. A plunger 60 is carried by and movable with respect to the retention module 56. The plunger 60 carries a pin 62 aligned with the hole 58 in the retention module 56. The pin 62 ejects the electrode 10 when the retention module 56 and the plunger 60 move toward each other to enable the pin 62 to enter the hole 58 where the electrode 10 is seated. The plunger 60 has a spring 68, made of radially outwardly biased legs that interact with the retention module 56 by resisting their relative movement. The plunger 60 loads the spring 68 as the retention module 56 presses against the skin of a patient, so that a predetermined pressure against the skin is required before the electrode 10 ejects from the applicator 20.

A magazine 12 hold plural applicators 20, such as the six shown, and the electrode 10 carried by each one of them is applied in sequence, each applicator 20 being expelled after its electrode 10 is ejected, and the next applicator 20 moved into position at first end 14 of the magazine 12 in rapid sequence.

FIG. 1 is a partial, perspective left side view of the present magazine 12 with an applicator 20 presenting with its electrode 10 and lead wire visible.

FIG. 2 is a partial, perspective, right side closer view of the present magazine 12 shown in FIG. 1.

FIG. 3 is a perspective right side partially cut away view of the magazine 12 to show the row of applicators 20 and the components of the actuator 30.

FIG. 4 is a partial, perspective, right side closer view of the present magazine 12 shown in FIG. 2 with the electrode 10 ejected from the retention module of the applicator 20.

FIG. 5 shows an applicator 20 without an electrode 10.

FIG. 6 is a cross sectional view of an applicator 20 to show the retention module and the plunger.

Figure 7:
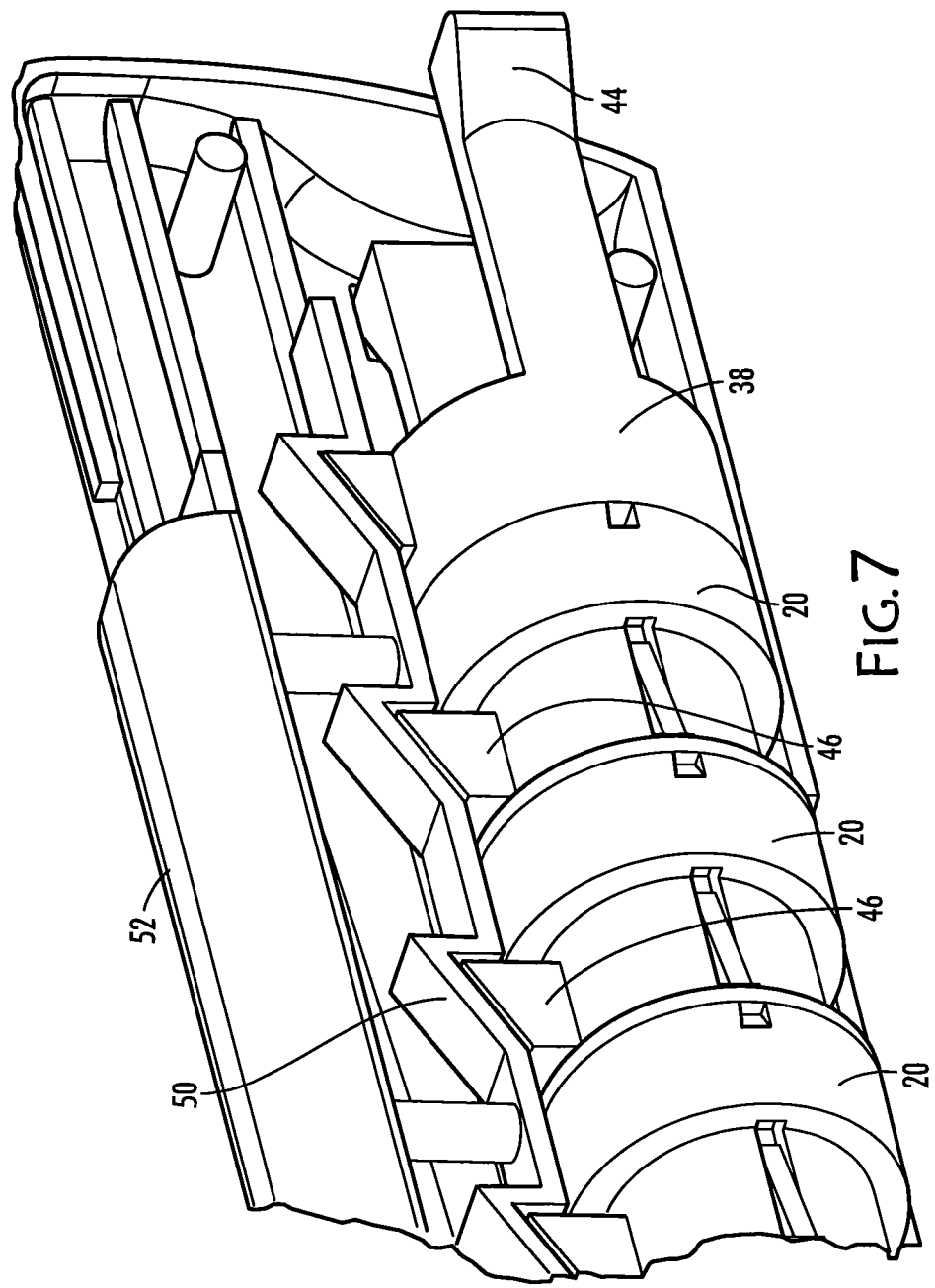
FIG. 7 is a perspective view of the stopper at the end of a row of applicators, according to an embodiment of the invention.

FIG. 7 is a perspective view of the stopper 38 at the end of a row of applicators 20.

Figure 8:
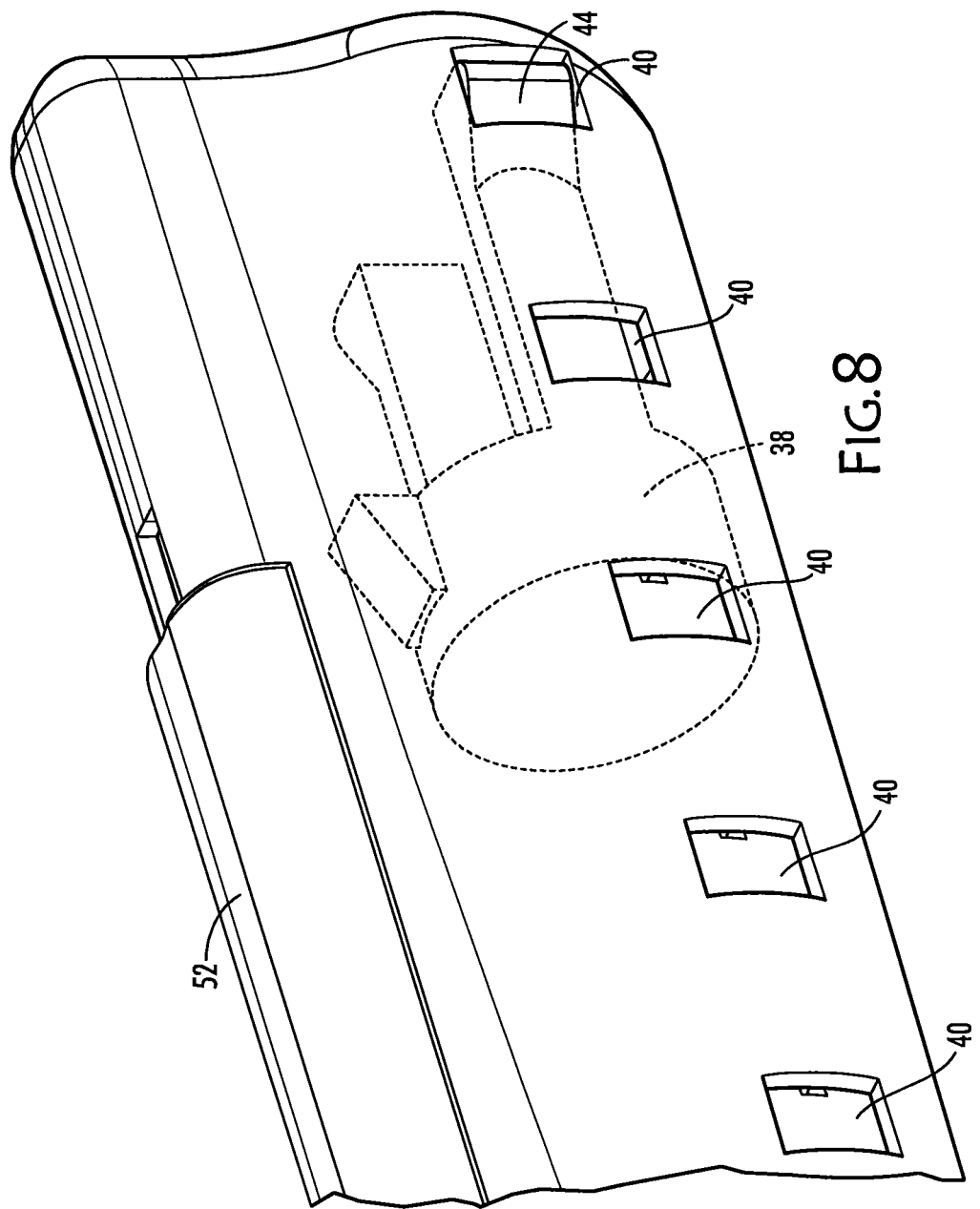
FIG. 8 is a perspective view of the second end of the magazine with the stopper presented in phantom lines, according to an embodiment of the invention.

FIG. 8 is a perspective view of the second end of the magazine 12 with the stopper 38 presented in phantom lines to show its interaction with the catches on the interior of the magazine 12.

FIG. 9 is a bottom view of the magazine 12 showing the channel through which the lead wires of the row of applicators 20 hang.

What is claimed is:

1. A system for inserting a series of subdermal electrodes into the skin of a patient for neurological monitoring, said system comprising:
    (a) a magazine with an interior, a major axis and a first end and an opposing second end, said first end having an opening;
    (b) plural applicators carried in the interior of said magazine in a row and in parallel with said major axis, said plural applicators including a previous applicator followed by a subsequent applicator, said previous applicator having a first end and an opposing second end, said subsequent applicator having a first end and an opposing second end, said first end of said previous applicator presenting at said opening of said magazine;
    (c) plural electrodes, each electrode of said plural electrodes being releasably carried by one applicator of said plural applicators so that said each electrode is ejected from said one applicator when said one applicator is pressed against the skin of a patient; and
    (d) an actuator carried by said magazine, said actuator advancing said plural applicators in sequence and axially toward said opening of said magazine to expel said previous applicator through said opening and to present said subsequent applicator,
    wherein each applicator of said plural applicators has a dog and said actuator has a dog-engaging bar movable axially, said dog-engaging bar moving only axially toward said first end of said magazine and moving radially outward and axially as said dog-engaging bar is moved toward said second end of said magazine and said dog-engaging bar is cammed by said dog of said each applicator.

2. The system as recited in claim 1 further comprising a stopper carried in said magazine at said second end and aligned with said row of said plural applicators, said stopper being moveable toward said first end of said magazine but not rearward toward said second end of said magazine.

3. The system as recited in claim 2, wherein said stopper moves in increments so that said previous applicator is ejected and said first end of said subsequent applicator is presented at said opening in each increment.

4. The system as recited in claim 2, wherein said stopper has two radially-opposing, radially-biased feet and said magazine has plural catches dimensioned to receive and hold said feet against movement rearward toward said second end of said magazine as said stopper is moved axially forward toward said first end of said magazine.

5. The system as recited in claim 1, wherein said actuator includes a slide carried exterior to said magazine and in operative connection with said dog-engaging bar interior to said magazine to move said plural applicators.

6. The system as recited in claim 1, wherein said magazine has an axial channel formed therein and wherein said each electrode includes a lead wire, said lead wire hanging through said channel.

7. The system as recited in claim 1, wherein said each applicator of said plural applicators includes a retention module with a hole formed therein for holding said each electrode inserted into said hole, and a plunger movable with respect to said retention module, said plunger having a pin aligned with said hole of said retention module, said pin ejecting said each electrode held in said hole when said retention module and said pin move.

8. The system as recited in claim 7, wherein said plunger has a spring interactive with said retention module by resisting relative movement of said plunger and said retention module, said plunger loading said spring as said retention module presses against the skin of a patient.

* * * * *